US011702581B2

(12) United States Patent
Pisklak et al.

(10) Patent No.: US 11,702,581 B2
(45) Date of Patent: Jul. 18, 2023

(54) REACTIVITY MAPPING

(71) Applicant: Halliburton Energy Services, Inc., Houston, TX (US)

(72) Inventors: Thomas Jason Pisklak, Cypress, TX (US); James Robert Benkley, Duncan, OK (US); Darrell Chad Brenneis, Marlow, OK (US); Ronnie Glen Morgan, Waurika, OK (US); Walmy Cuello Jimenez, Houston, TX (US); John P. Singh, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 949 days.

(21) Appl. No.: 16/479,848

(22) PCT Filed: Feb. 22, 2017

(86) PCT No.: PCT/US2017/018953
§ 371 (c)(1),
(2) Date: Jul. 22, 2019

(87) PCT Pub. No.: WO2018/156124
PCT Pub. Date: Aug. 30, 2018

(65) Prior Publication Data
US 2020/0332172 A1  Oct. 22, 2020

(51) Int. Cl.
*C09K 8/46* (2006.01)
*G16C 20/30* (2019.01)
(Continued)

(52) U.S. Cl.
CPC ............... *C09K 8/46* (2013.01); *C04B 28/02* (2013.01); *E21B 33/138* (2013.01); *E21B 33/14* (2013.01); *G16C 20/30* (2019.02); *G16C 60/00* (2019.02)

(58) Field of Classification Search
CPC .......... C09K 8/46; C09K 8/467; C04B 28/02; C04B 28/04; E21B 33/13; E21B 33/138; E21B 33/14; G16C 20/30; G16C 60/00
See application file for complete search history.

(56) References Cited

U.S. PATENT DOCUMENTS

| 7,395,860 B2 | 7/2008 | Roddy et al. |
| 7,607,484 B2 | 10/2009 | Roddy et al. |

(Continued)

FOREIGN PATENT DOCUMENTS

| CN | 104812868 | 7/2015 |
| CN | 104822796 | 8/2015 |

(Continued)

OTHER PUBLICATIONS

"Determination of particle size, surface area, and shape of supplementary cementitious materials by different techniques", Arvaniti, et al., Materials and Structures, 2015, 48:3687-3701 (Year: 2015).*

(Continued)

*Primary Examiner* — Aiqun Li
(74) *Attorney, Agent, or Firm* — Thomas Rooney; C. Tumey Law Group PLLC

(57) ABSTRACT

Reactivity mapping methods are provided. A method may include: analyzing each of a group of inorganic particles to generate data about physical and/or chemical properties of the inorganic particles; and generating correlations between the properties of inorganic particles based on the data.

25 Claims, 3 Drawing Sheets

(51) Int. Cl.
*G16C 60/00* (2019.01)
*C04B 28/02* (2006.01)
*E21B 33/138* (2006.01)
*E21B 33/14* (2006.01)

(56) References Cited

U.S. PATENT DOCUMENTS

| | | |
|---|---|---|
| 7,631,692 B2 | 12/2009 | Roddy et al. |
| 7,806,183 B2 | 10/2010 | Roddy et al. |
| 7,892,352 B2 | 2/2011 | Roddy et al. |
| 8,281,859 B2 | 10/2012 | Roddy et al. |
| 8,333,240 B2 | 12/2012 | Roddy et al. |
| 8,486,869 B2 | 7/2013 | Brenneis et al. |
| 8,609,592 B2 | 12/2013 | Guenthenspberger et al. |
| 8,609,595 B2 | 12/2013 | Morgan et al. |
| 8,851,173 B2 | 10/2014 | Brothers et al. |
| 8,997,578 B2 | 4/2015 | Morgan et al. |
| 9,023,150 B2 | 5/2015 | Brenneis et al. |
| 9,212,534 B2 | 12/2015 | Ballew et al. |
| 9,505,972 B2 | 11/2016 | Iverson et al. |
| 9,644,132 B2 | 5/2017 | Morgan et al. |
| 10,370,579 B2 | 8/2019 | Agapiou et al. |
| 11,174,198 B2 | 11/2021 | Morgan et al. |
| 2010/0224365 A1 | 9/2010 | Abad |
| 2013/0048286 A1* | 2/2013 | Morgan ............... C04B 28/02 |
| | | 106/638 |
| 2015/0024976 A1 | 1/2015 | Albrighton et al. |
| 2015/0184060 A1 | 7/2015 | Morgan et al. |
| 2015/0321953 A1 | 11/2015 | Porcherie |
| 2017/0364607 A1 | 12/2017 | Kaushik et al. |

FOREIGN PATENT DOCUMENTS

| | | |
|---|---|---|
| RU | 2616959 | 4/2017 |
| WO | 2016122531 | 8/2016 |

OTHER PUBLICATIONS

Russian Office Action and Search Report with Partial Translation for Application No. 2019121899 dated Feb. 21, 2020.
ISRWO International Search Report and Written Opinion for PCT/US2017/018953 dated Nov. 22, 2017.
Chinese Office Action and Search Report for CN Application No. 2017800833888 dated Dec. 3, 2020.

* cited by examiner

REACTIVITY MAPPING

BACKGROUND

In well cementing, such as well construction and remedial cementing, cement compositions are commonly utilized. Cement compositions may be used in a variety of subterranean applications. For example, in subterranean well construction, a pipe string (e.g., casing, liners, expandable tubulars, etc.) may be run into a well bore and cemented in place. The process of cementing the pipe string in place is commonly referred to as "primary cementing." In a typical primary cementing method, a cement composition may be pumped into an annulus between the walls of the well bore and the exterior surface of the pipe string disposed therein. The cement composition may set in the annular space, thereby forming an annular sheath of hardened, substantially impermeable cement (i.e., a cement sheath) that may support and position the pipe string in the well bore and may bond the exterior surface of the pipe string to the subterranean formation. Among other things, the cement sheath surrounding the pipe string functions to prevent the migration of fluids in the annulus, as well as protecting the pipe string from corrosion. Cement compositions also may be used in remedial cementing methods, for example, to seal cracks or holes in pipe strings or cement sheaths, to seal highly permeable formation zones or fractures, to place a cement plug, and the like.

A particular challenge in well cementing is the development of satisfactory mechanical properties in a cement composition within a reasonable time period after placement in the subterranean formation. Oftentimes several cement compositions with varying additives are tested to see if they meet the material engineering requirements for a particular well. The process of selecting the components of the cement composition are usually done by a best guess approach by utilizing previous slurries and modifying them until a satisfactory solution is reached. The process may be time consuming and the resulting slurry may be expensive. Furthermore, the cement components available in any one particular region may vary in composition from those of another region thereby further complicating the process of selecting a correct slurry.

BRIEF DESCRIPTION OF THE DRAWINGS

These drawings illustrate certain aspects of some of the embodiments of the present invention, and should not be used to limit or define the invention.

DETAILED DESCRIPTION

Figure 1:
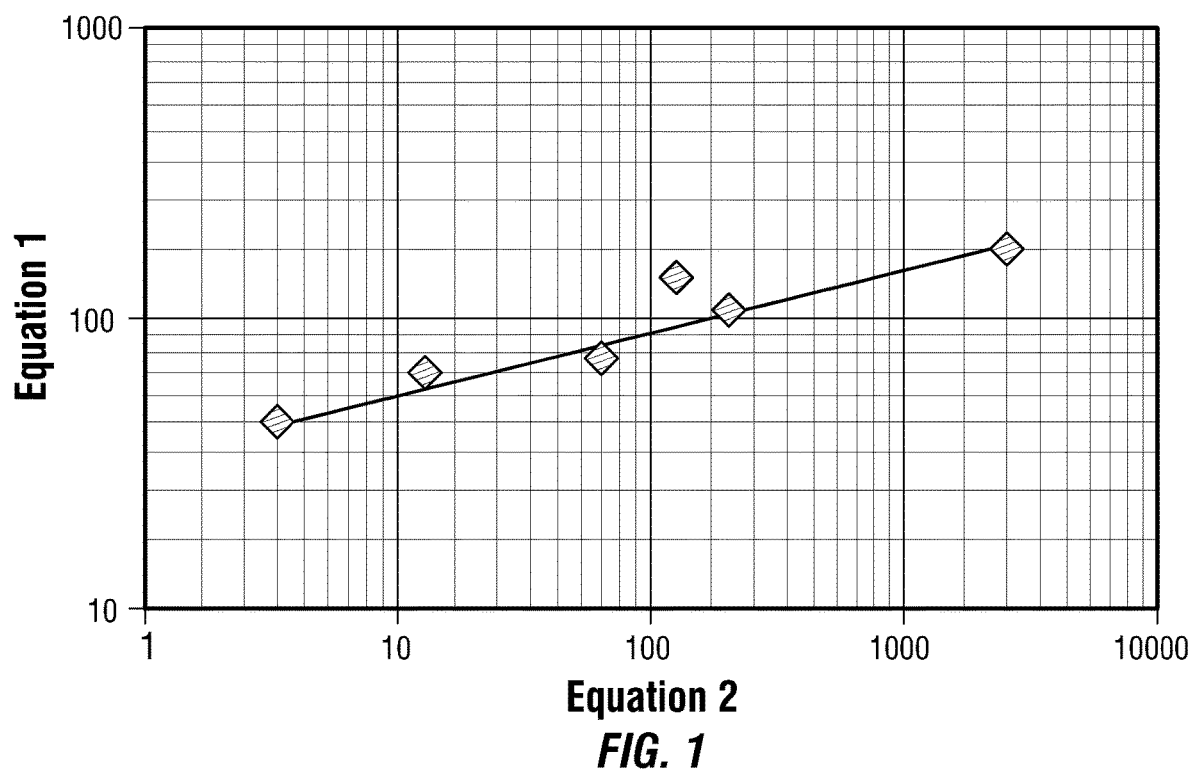
FIG. 1 is a chart showing simulated results for compressive strength index calculations.

The present disclosure may generally relate to cementing methods and system. Provided herein are methods that may include identifying and categorizing silica sources, cements, and other materials based on physicochemical properties. In some examples, the silica sources may be considered inorganic particles. The inorganic particles may or may not comprise silica and may comprise other minerals such as alumina and other oxides. The physicochemical properties of each cement component of a cement composition may affect the final set mechanical properties of the slurry as well as the dynamic or time based properties such as mixability, rheology, viscosity, and others. Every cement component may affect one or more of the properties mentioned, sometimes unpredictably. For example, a locally sourced fly ash may be added to a cement composition. The added fly ash may increase the compressive strength of the cement composition and may have no effect on for example, the thickening time of the cement composition. In another region, a locally sourced fly ash may also increase the compressive strength of the cement composition but may also increase the thickening time. The unpredictable behavior of a cement composition may not be realized until multiple lab tests have been performed.

The cement compositions generally may comprise water and a cement additive. The cement additive may comprise two or more cement components, which may be dry blended to form the cement additive prior to combination with the water. Alternatively, the cement components may not be combined until mixture with the water. The cement components may generally be described as alkali soluble.

The cement components may also be cementitious in nature. A cement composition may comprise water and a cement additive, such as, hydraulic cement, cement kiln dust, and/or a natural pozzolan, among others. As described in more detail herein, the cement compositions may be foamed and/or extended as desired by those of ordinary skill in the art.

The cement compositions may have a density suitable for a particular application. The cement compositions may have any suitable density, including, but not limited to, in the range of about 8 pounds per gallon ("ppg") to about 16 ppg (1 g/cm$^3$ to 1.9 g/cm$^3$). In the foamed examples, the cement compositions may have a density in the range of about 8 ppg to about 13 ppg (1 g/cm$^3$ to 1.6 g/cm$^3$) (or even lower).

The water used in the cement compositions may include, for example, freshwater, saltwater (e.g., water containing one or more salts dissolved therein), brine (e.g., saturated saltwater produced from subterranean formations), seawater, or combinations thereof. Generally, the water may be from any source, provided that it does not contain an excess of compounds that may undesirably affect other components in the cement composition. The water may be included in an amount sufficient to form a pumpable slurry. The water may be included in the cement compositions in any suitable range, including, but not limited to, in the range of about 40% to about 200% by weight of the cement additive ("bwoc"). In some examples, the water may be included in an amount in the range of about 40% to about 150% bwoc.

The cement additive may comprise two or more cement components. One of the cement components may comprise a hydraulic cement. A variety of hydraulic cements may be utilized in accordance with the present disclosure, including, but not limited to, those comprising calcium, aluminum, silicon, oxygen, iron, and/or sulfur, which set and harden by reaction with water. Suitable hydraulic cements may include Portland cements, gypsum, and high alumina content cements, among others. Portland cements that are suited for use in the present disclosure may be classified as Classes A, C, G, and H cements according to American Petroleum Institute, API Specification for Materials and Testing for Well Cements, API Specification 10, Fifth Ed., Jul. 1, 1990. In addition, in some examples, cements suitable for use in the present invention may be classified as ASTM Type I, II, or III. Cement compositions that may be considered "low Portland" may be designed by use of the techniques disclosed herein.

Where present, the hydraulic cement generally may be included in the cement compositions in an amount sufficient to provide the desired compressive strength, density, and/or cost. The hydraulic cement may be present in the cement compositions in any suitable amount, including, but not limited to, in the range of about 0% to about 99% bwoc. In some examples the hydraulic cement may be present in an amount ranging between any of and/or including any of about 1%, about 5%, about 10%, about 20%, about 40%, about 60%, about 80%, or about 90% bwoc. Cement composition that are considered "low Portland" may be used, in that the Portland cement (where used) may be present in the cement composition in an amount of about 40% or less bwoc and, alternatively, about 10% or less. In addition, the cement compositions may also be designed that are free (or essentially free) of Portland cement. Those of ordinary skill in the art, with the benefit of this disclosure, should be able to select an appropriate amount of hydraulic cement for a particular application.

In addition to Portland cement, additional cement components may be used that can be considered alkali soluble. A cement component is considered alkali soluble where it is at least partially soluble in an aqueous solution of pH 7.0 or greater. Certain of the alkali soluble cement components may comprise a geopolymer cement, which may comprise an aluminosilicate source, a metal silicate source, and an activator. The geopolymer cement may react to form a geopolymer. A geopolymer is an inorganic polymer that forms long-range, covalently bonded, non-crystalline networks. Geopolymers may be formed by chemical dissolution and subsequent re-condensation of various aluminosilicates and silicates to form a 3D-network or three-dimensional mineral polymer.

The activator for the geopolymer cement may include, but is not limited to, metal hydroxides chloride salts such as KCl, $CaCl_2$, NaCl, carbonates such as $Na_2CO_3$, silicates such as sodium silicate, aluminates such as sodium aluminate, and ammonium hydroxide.

The aluminosilicate source for the geopolymer cement may comprise any suitable aluminosilicate. Aluminosilicate is a mineral comprising aluminum, silicon, and oxygen, plus counter-cations. There are potentially hundreds of suitable minerals that may be an aluminosilicate source in that they may comprise aluminosilicate minerals. Each aluminosilicate source may potentially be used in a particular case if the specific properties, such as composition, may be known. Some minerals such as andalusite, kyanite, and sillimanite are naturally occurring aluminosilicate sources that have the same composition, $Al_2SiO_5$, but differ in crystal structure. Each mineral andalusite, kyanite, or sillimanite may react more or less quickly and to different extents at the same temperature and pressure due to the differing crystal structures. Other suitable aluminosilicate sources may include, but are not limited to, calcined clays, partially calcined clays, kaolinite clays, lateritic clays, illite clays, volcanic rocks, mine tailings, blast furnace slag, and coal fly ash.

The metal silicate source may comprise any suitable metal silicate. A silicate is a compound containing an anionic silicon compound. Some examples of a silicate include the orthosilicate anion also known as silicon tetroxide anion, $SiO_4^{4-}$ as well as hexafluorosilicate $[SiF_6]^{2-}$. Other common silicates include cyclic and single chain silicates which may have the general formula $[SiO_{2+n}]^{2n-}$ and sheet-forming silicates $([SiO_{2.5}]^-)_n$. Each silicate example may have one or more metal cations associated with each silicate molecule. Some suitable metal silicate sources and may include, without limitation, sodium silicate, magnesium silicate, and potassium silicate.

Where present, the geopolymer cement generally may be included in the cement compositions in an amount sufficient to provide the desired compressive strength, density, and/or cost. The geopolymer cement may be present in the cement compositions in any suitable amount, including, but not limited to, an amount in the range of about 0% to about 99% bwoc. In some examples the geopolymer cement may be present in an amount ranging between any of and/or including any of about 1%, about 5%, about 10%, about 20%, about 40%, about 60%, about 80%, or about 90% bwoc. Those of ordinary skill in the art, with the benefit of this disclosure, should be able to select an appropriate amount of geopolymer cement for a particular application.

Additional cement components that are alkali soluble may be considered a silica source. As used herein, silica has the plain and ordinary meaning of silicon dioxide ($SiO_2$). By inclusion of the silica source, a different path may be used to arrive at a similar product as from Portland cement. For example, a pozzolanic reaction may be induced wherein silicic acid ($H_4SiO_4$) and portlandite ($Ca(OH)_2$ react to form a cement product (calcium silicate hydrate). If other compounds, such as, aluminate, are present in the silica source, additional reactions may occur to form additional cement products, such as calcium aluminate hydrates. Additionally, alumina may be present in the silica source. As used herein, alumina is understood to have the plain and ordinary meaning of aluminum oxide ($Al_2O_3$). Calcium hydroxide necessary for the reaction may be provide from other cement components, such as Portland cement, or may be separately added to the cement composition. Examples of suitable silica sources may include fly ash, slag, silica fume, crystalline silica, silica flour, cement kiln dust ("CKD"), volcanic rock, perlite, metakaolin, diatomaceous earth, zeolite, shale, and agricultural waste ash (e.g., rice husk ash, sugar cane ash, and bagasse ash), among other. Some specific examples of the silica source will be discussed in more detail below. Where present, the silica source generally may be included in the cement compositions in an amount sufficient to provide the desired compressive strength, density, and/or cost. The silica source may be present in the cement compositions in any suitable amount, including, but not limited to an amount in the range of about 0% to about 99% bwoc. In some examples the silica source may be present in an amount ranging between any of and/or including any of about 1%, about 5%, about 10%, about 20%, about 40%, about 60%, about 80%, or about 90% bwoc. Those of ordinary skill in the art, with the benefit of this disclosure, should be able to select an appropriate amount of silica source for a particular application.

Amorphous silica may also be present. Amorphous silica may prevent strength retrogression. In general, amorphous silica may not require temperatures above 235° F. to participate in cement hydrations. Amorphous silica may protect against strength retrogression and maximize design efficiency by eliminating the need for multiple designs at different temperatures. Amorphous silica may also replace crystalline silica in some applications.

An example of a suitable silica source may comprise fly ash. A variety of fly ash may be suitable, including fly ash classified as Class C and Class F fly ash according to American Petroleum Institute, API Specification for Materials and Testing for Well Cements, API Specification 10, Fifth Ed., Jul. 1, 1990. Class C fly ash comprises both silica and lime, so it may set to form a hardened mass upon mixing with water. Class F fly ash generally does not contain a sufficient amount of lime to induce a cementitious reaction, therefore, an additional source of calcium ions is necessary for a set-delayed cement composition comprising Class F fly ash. In some embodiments, lime may be mixed with Class F fly ash in an amount in the range of about 0.1% to about 100% by weight of the fly ash. In some instances, the lime may be hydrated lime. Suitable examples of fly ash include, but are not limited to, POZMIX® A cement additive, commercially available from Halliburton Energy Services, Inc., Houston, Tex.

Another example of a suitable silica source may comprise slag. Slag is generally a by-product in the production of various metals from their corresponding ores. By way of example, the production of cast iron can produce slag as a granulated, blast furnace by-product with the slag generally comprising the oxidized impurities found in iron ore. Slag generally does not contain sufficient basic material, so slag cement may be used that further may comprise a base to produce a settable composition that may react with water to set to form a hardened mass. Examples of suitable sources of bases include, but are not limited to, sodium hydroxide, sodium bicarbonate, sodium carbonate, lime, and combinations thereof.

Another example of a suitable silica source may comprise CKD. Cement kin dust or "CKD", as that term is used herein, refers to a partially calcined kiln feed which is removed from the gas stream and collected, for example, in a dust collector during the manufacture of cement. Usually, large quantities of CKD are collected in the production of cement that are commonly disposed of as waste. Disposal of the CKD as waste can add undesirable costs to the manufacture of the cement, as well as the environmental concerns associated with its disposal. CKD is another component that may be included in examples of the cement compositions.

Another example of a suitable silica source may comprise volcanic rock. Certain volcanic rocks may exhibit cementitious properties, in that it may set and harden in the presence of hydrated lime and water. The volcanic rock may also be ground, for example. Generally, the volcanic rock may have any particle size distribution as desired for a particular application. In certain embodiments, the volcanic rock may have a mean particle size in a range of from about 1 micron to about 200 microns. The mean particle size corresponds to d50 values as measured by particle size analyzers such as those manufactured by Malvern Instruments, Worcestershire, United Kingdom. One of ordinary skill in the art, with the benefit of this disclosure, should be able to select a particle size for the volcanic rock suitable for a chosen application.

Another example of a suitable silica source may comprise metakaolin. Generally, metakaolin is a white pozzolan that may be prepared by heating kaolin clay, for example, to temperatures in the range of about 600° to about 800° C.

Another example of a suitable silica source may comprise shale. Among other things, shale included in the cement compositions may react with excess lime to form a suitable cementing material, for example, calcium silicate hydrate. A variety of shales are suitable, including those comprising silicon, aluminum, calcium, and/or magnesium. An example of a suitable shale comprises vitrified shale. Generally, the shale may have any particle size distribution as desired for a particular application. In certain embodiments, the shale may have a particle size distribution in the range of about 37 micrometers to about 4,750 micrometers.

Another example of a suitable silica source may comprise zeolite. Zeolites generally are porous alumino-silicate minerals that may be either a natural or synthetic material. Synthetic zeolites are based on the same type of structural cell as natural zeolites, and may comprise aluminosilicate hydrates. As used herein, the term "zeolite" refers to all natural and synthetic forms of zeolite. Examples of zeolites may include, without limitation, mordenite, zsm-5, zeolite x, zeolite y, zeolite a, etc. Furthermore, examples comprising zeolite may comprise zeolite in combination with a cation such as $Na^+$, $K^+$, $Ca^{2+}$, $Mg^{2+}$, etc. Zeolites comprising cations such as sodium may also provide additional cation sources to the cement composition as the zeolites dissolve.

The cement compositions may further comprise hydrated lime. As used herein, the term "hydrated lime" will be understood to mean calcium hydroxide. In some examples, the hydrated lime may be provided as quicklime (calcium oxide) which hydrates when mixed with water to form the hydrated lime. The hydrated lime may be included in examples of the cement compositions, for example, to form a hydraulic composition with the silica source. For example, the hydrated lime may be included in a silica source-to-hydrated-lime weight ratio of about 10:1 to about 1:1 or a ratio of about 3:1 to about 5:1. Where present, the hydrated lime may be included in the cement compositions in an amount in the range of from about 10% to about 100% by weight of the silica source, for example. In some examples, the hydrated lime may be present in an amount ranging between any of and/or including any of about 10%, about 20%, about 40%, about 60%, about 80%, or about 100% by weight of the silica source. One of ordinary skill in the art, with the benefit of this disclosure, should recognize the appropriate amount of hydrated lime to include for a chosen application.

In some examples, the cement compositions may comprise a calcium source other than hydrated lime. In general, calcium and a high pH, for example a pH of 7.0 or greater, may be needed for certain cementitious reactions to occur. A potential advantage of hydrated lime may be that calcium ions and hydroxide ions are supplied in the same molecule. In another example, the calcium source may be $Ca(NO_3)_2$ or $CaCl_2$ with the hydroxide being supplied form NaOH or KOH, for example. One of ordinary skill would understand the alternate calcium source and hydroxide source may be included in a cement composition in the same way as hydrated lime. For example, the calcium source and hydroxide source may be included in a silica source-to-hydrated-lime weight ratio of about 10:1 to about 1:1 or a ratio of about 3:1 to about 5:1. Where present, the alternate calcium source and hydroxide source may be included in the cement compositions in an amount in the range of from about 10% to about 100% by weight of the silica source, for example. In some examples, the alternate calcium source and hydroxide source may be present in an amount ranging between any of and/or including any of about 10%, about 20%, about 40%, about 60%, about 80%, or about 100% by weight of the silica source. One of ordinary skill in the art, with the benefit of this disclosure, should recognize the appropriate amount of alternate calcium source and hydroxide source to include for a chosen application.

A target silica lime ratio may be defined and a cement additive comprising two or more cement components may be identified that meets the silica lime ratio. In some examples, the target silica lime ratio may range from about 80/20 silica to free lime by weight to about 60/40 silica to free lime by weight, for example, be about 80/20 silica to free lime by weight, about 70/30 silica to free lime by weight, or about 60/40 silica to free lime by weight. The silica lime ratio may be determined by measuring the available silica and lime for a given cement component.

Other additives suitable for use in cementing operations also may be included in embodiments of the cement compositions. Examples of such additives include, but are not limited to: weighting agents, retarders, accelerators, activators, gas control additives, lightweight additives, gas-generating additives, mechanical-property-enhancing additives, lost-circulation materials, filtration-control additives, fluid-loss-control additives, defoaming agents, foaming agents, dispersants, thixotropic additives, suspending agents, and combinations thereof. One of ordinary skill in the art, with the benefit of this disclosure, should be able to select an appropriate additive for a particular application.

As mentioned previously, in order to determine if two or more of the aforementioned cement components are compatible, several lab tests may be run. Additionally, any potential synergistic effects of the cement component may not be known unless several laboratory tests are performed. Typically, a known cement composition may be first formulated and tested for properties such as, for example, the 24 hour compressive strength, fluid loss, and thickening time. Then, varying amounts of additives may be added to a fresh batch of cement compositions and the tests are re-run. The results are gathered form each test and compared. A new set of tests may then be run with new concentrations of additives, for example, to adjust properties of the cement composition. The process of testing various additives in varying concentrations may go on for several trials until an acceptable cement composition or compositions is formulated. An acceptable cement composition may be one that meets certain design requirements, such as compressive strength, fluid loss, and thickening time. The cement composition design process may be done in a heuristic manner leading to a cement composition that may have the required engineering properties but may not be optimized for cost. Additionally, silica sources such as, for example, CKD, have been previously used as either pure fillers or in some examples, reactive components, in Portland based cement compositions. CKD will contribute a portion of silica which requires a portion of lime to react. In methods of cement composition formulation described above, the heuristic process does not take into account the silica to lime ratio of a composition.

The method described herein may reduce or eliminate the heuristic search for by a process that identifies a cement additive through a process of measuring and categorizing a variety of cement components referred to as reactivity mapping. Reactivity mapping may generate a correlation between properties of inorganic particles. Reactivity mapping may comprise several steps. One step may comprise measuring the physical and chemical properties of different materials through standardized tests. Another step may comprise categorizing the materials through analysis of data collected and the predicted effect on cement slurry properties. Yet another step may comprise utilizing the data to estimate material reactivity, improve cement performance, predicting blend mechanical properties mathematically based on analytical results, and/or predict slurry density dependence of compressive strength.

Measuring physical and chemical properties of each selected cement component may comprise many laboratory techniques and procedures including, but not limited to, microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological properties, Poisson's Ratio. One or more of the proceeding tests may be consider API tests, as set forth in the API recommended practice for testing well cements (published as ANSI/API recommended practice 10B-2). Additional API tests not specifically listed above may also be used for the measurements. The physical and chemical properties may be measured for a group of cement components. Two or more of the cement components measured may be different types of cement components (e.g., volcanic rock, CKD, fly ash, etc.). Two or more of the cement components may be the same type but from different sources (e.g., volcanic rock from source 1, volcanic rock from source 2, etc.).

X-ray powder diffraction is one analysis technique that may be used for measuring the physical and chemical properties of the cement components. X-ray powder diffraction is a technique of exposing a sample to x-rays, neutrons, or electrons and measuring the amount of inter-atomic-diffraction. The sample acts a diffraction grating thereby producing a differing signal at different angles. The typical properties that may be measured are the phase identification for the identification and characterization of a crystalline solid. Other properties may be crystallinity, lattice parameters, expansion tensors, bulk modulus, and phase transitions.

X-ray fluorescence is another analysis technique that may be used for measuring the physical and chemical properties of the cement components. X-ray fluorescence may use short wave x-rays to ionize atoms in a sample thereby causing them to fluoresce at certain characteristic wavelengths. The characteristic radiation released by a sample may allow accurate identification of the component atoms in the sample as well as their relative amounts.

Particle size analysis is another analysis technique that may be used for measuring the physical and chemical properties of the cement components. Particle size analysis may be accomplished through analysis by various laboratory techniques including but not limited to laser diffraction, dynamic light scattering, static image analysis, and dynamic image analysis. Particle size analysis may also provide information about the morphology of a particular sample. Morphology may include parameters such as sphericity and roundness as well as the general shape of a particle such as disk, spheroid, blade, or roller. With a knowledge of the morphology and particle size, the average surface area and volume may be estimated. Surface area and volume may be important in determining the water requirement as well as reactivity. In general, a relatively smaller particle size may react more quickly than a relatively larger particle size. Also the relatively smaller particle size may have a greater water requirement to completely hydrate than a relatively larger particle size.

Energy dispersive x-ray spectroscopy is another analysis technique that may be used for measuring the physical and chemical properties of the waste materials. Energy dispersive x-ray spectroscopy is an analytical technique used to analyze the elements present in a sample and determine the chemical characterization of a sample. Other techniques may include Fourier transform infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma mass spectrometry (ICP-MS), thermal ionization mass spectroscopy, glow discharge mass spectroscopy, and x-ray photoelectron spectroscopy.

The cement components may be analyzed to determine their water requirement. Water requirement is typically defined as the amount of mixing water that is required to be added to a powdered, solid material to form a slurry of a specified consistency. Water requirement for a particular cement component may be determined by a process that includes a) preparing a Waring blender with a specified amount of water, b) agitating the water at a specified blender rpm, c) adding the powdered solid that is being investigated to the water until a specified consistency is obtained, and d) calculating the water requirement based on the ratio of water to solids required to reach the desired consistency.

The cement components may be analyzed to determine their specific surface area. Specific surface area generally refers to the total surface area and may be reported as the total surface area per unit mass. Values obtained for specific area are dependent on the analysis technique. Any suitable analysis technique may be used, including without limitation adsorption based methods such as Brunauer-Emmett-Teller (BET) analysis, methylene blue staining, ethylene glycol monoethyl ether adsorption, and a protein-retention method, among other.

Thermogravimetric analysis is another analysis technique that may be used for measuring the physical and chemical properties of the cement components. Thermogravimetric analysis is a method of thermal analysis wherein changes in physical and chemical properties of a sample may be measured. In general the properties may be measured as a function of increasing temperature, such as with a constant heating rate, or as a function of time with a constant temperature or a constant mass change. Properties determined by thermogravimetric analysis may include first-order phase transitions and second-order phase transitions such as vaporization, sublimation, adsorption, desorption, absorption, chemisorption, desolvation, dehydration, decomposition, oxidation and reduction reactions, ferromagnetic transition, superconducting transition, and others.

In addition to determining physical and chemical properties of the cement components themselves, laboratory tests may also be run to determine behavior of the cement components in a cement composition. For example, the cement components may be analyzed in a cement composition to determine their compressive strength development and mechanical properties. For example, a preselected amount of the cement component may be combined with water and lime (if needed for setting). The mechanical properties of the cement composition may then be determined including, compressive strength, tensile strength, and Young's modulus. Any of a variety of different conditions may be used for the testing so long as the conditions are consistent for the different cement components.

Compressive strength is generally the capacity of a material or structure to withstand axially directed pushing forces. The compressive strength of the cement component may be measured at a specified time after the cement component has been mixed with water and the resultant cement composition is maintained under specified temperature and pressure conditions. For example, compressive strength can be measured at a time in the range of about 24 to about 48 hours (or longer) after the fluid is mixed and the fluid is maintained at a temperature of from 100° F. to about 200° F. and atmospheric pressure. Compressive strength can be measured by either a destructive method or non-destructive method. The destructive method physically tests the strength of treatment fluid samples at various points in time by crushing the samples in a compression-testing machine. The compressive strength is calculated from the failure load divided by the cross-sectional area resisting the load and is reported in units of pound-force per square inch (psi). Non-destructive methods typically may employ an Ultrasonic Cement Analyzer ("UCA"), available from Fann® Instrument Company, Houston, Tex. Compressive strengths may be determined in accordance with API RP 10B-2, *Recommended Practice for Testing Well Cements*, First Edition, July 2005.

Tensile strength is generally the capacity of a material to withstand loads tending to elongate, as opposed to compressive strength. The tensile strength of the cement component may be measured at a specified time after the cement component has been mixed with water and the resultant cement composition is maintained under specified temperature and pressure conditions. For example, tensile strength can be measured at a time in the range of about 24 to about 48 hours (or longer) after the fluid is mixed and the fluid is maintained at a temperature of from 100° F. to about 200° F. and atmospheric pressure. Tensile strength may be measured using any suitable method, including without limitation in accordance with the procedure described in ASTM C307. That is, specimens may be prepared in briquette molds having the appearance of dog biscuits with a one square inch cross-sectional area at the middle. Tension may then be applied at the enlarged ends of the specimens until the specimens break at the center area. The tension in pounds per square inch at which the specimen breaks is the tensile strength of the material tested.

Young's modulus also referred to as the modulus of elasticity is a measure of the relationship of an applied stress to the resultant strain. In general, a highly deformable (plastic) material will exhibit a lower modulus when the confined stress is increased. Thus, the Young's modulus is an elastic constant that demonstrates the ability of the tested material to withstand applied loads. A number of different laboratory techniques may be used to measure the Young's modulus of a treatment fluid comprising a cementitious component after the treatment fluid has been allowed to set for a period of time at specified temperature and pressure conditions.

Although only some select laboratory techniques may have been mentioned, it should be understood that there may be many analytical techniques that may be appropriate or not appropriate for a certain sample. One of ordinary skill in the art with the benefit of this disclosure should be able to select an appropriate analytical technique to determine a certain property of interest.

Once analytical techniques have been performed on the cement components, the data may be categorized and correlated. Some categories may include, but are not limited to, specific surface area, morphology, specific gravity, water requirement, etc. In some examples, the components may be categorized by relative amounts, including amount of at least one following: silica, alumina, iron, calcium, sodium, potassium, magnesium, sulfur, oxides thereof, and combinations thereof. For example, the components may be categorized based on an oxide analysis that includes without limitation, silica content, calcium oxide content, and alumina content among other oxides that may be present in the cement component. In addition, correlations between the cement components may be generated based on the data or categorization of the data. Additionally, correlations may be defined or generated between properties of the cement components based on the data. For example, the various categories of properties may be plotted against one another. In some examples, water requirement versus specific surface area may be plotted. Accordingly, the water requirement of the cement component may be correlated to the specific surface area so that the specific surface area is a function of water requirement. Specific surface area may be used to predict reactivity of a cement component (or components). However, specific surface area may not always be available for each material as specific surface area analysis typically requires a specialized instrument. Accordingly, if the water requirement may be obtained for the cement component, the correlation between water requirement and specific surface area may be used to obtain an estimate for specific surface area, which may then be used to predict reactivity. In addition to correlations between specific surface area and reactivity, correlations may also be made between specific surface area and other mechanical properties such as tensile strength and Young's modulus.

Some cement components that are alkali soluble may comprise reclaimed or natural materials. Specifically silica containing cement components may comprise materials such as mined materials, for example volcanic rock, perlite, waste materials, such as fly ash and CKD, and agricultural ashes as previously described. In some examples the cement component that is alkali soluble may have synergistic effects with a Portland cement while others may be incompatible. In some examples a cement component that is alkali soluble may cause gelation, high heat generation, water retention, among other effects. These and other effects may be realized during laboratory testing of the cement component in a cement composition comprising Portland cement. Laboratory equipment may be configured to detect the effects of the cement component on the composition. In some examples, equipment such a calorimeter may measure and quantify the amount of heat generation per unit mass of the cement component. Viscometers may measure the increase in gelation caused by the cement component. Each of the physical effects caused by the addition of the cement component may be measured at several concentrations and then categorized, e.g., plotted or mapped. Once a component is mapped, the effect of adding the component to a cement composition may be predicted by referencing the categorization.

As mentioned previously, some cement components that are alkali soluble may induce gelling when included in a cement composition. Although a higher gelling rate may be undesirable in some examples, in other examples, a higher gelling rate may be advantageous or necessary to meet the engineering design criteria. Usually one of ordinary skill in the art would select a suitable gelling agent or viscosifier for use in the cement composition. With the benefit of mapping, one of ordinary skill should be able to select a cement component that is alkali soluble that may serve a dual purpose. For example, a cement component may increase the compressive strength of a cement composition but also increase the gelling during mixing. If the engineering design criteria requires a higher gelling during mixing, it may be advantageous to include the cement component that increases the compressive strength while also increasing gelling. The inclusion of a cement component that exhibits multiple effects may reduce the amount of additional additives, such as gelling agents or viscosifiers, needed, which may be high cost. Since the component's gelling effect may have been documented in a map, the amount of component to include in a cement composition may be readily determined.

Another potentially advantageous physical effect that may be mapped is dispersing ability. Some cement components may comprise relatively spherical particles. The relatively spherical particles may exert a "roller bearing" effect in a cement composition with water. The effect may cause the other components in the cement composition to become more mobile thereby dispersing the components in the cement composition. If particles that are roughly $1/7^{th}$ or smaller than the primary component in a slurry, then the apparent viscosity may decrease. Another potentially advantageous physical property that may be mapped is surface area. Surface area may relate to density wherein a relatively higher surface area particle may lower the density of a cement composition. Particles which lower the density may be used as a low density additive. Another potentially advantageous effect that may be mapped is particle size. Components with relatively smaller particle sizes may have the ability to form a filter cake against a formation thereby blocking cement from escaping into a formation. Cement components with a small particle size may be used as a fluid loss control agent. With the benefit of the present disclosure, one of ordinary skill should be able to select a cement component and map its properties. One of ordinary skill should also be able to select a secondary property of interest of the cement component and with the benefit of the map, create a slurry with the desired properties.

Another potential benefit of replacing traditional cement additives with silica based cement components is a reduction in cost. A silica based cement component may partially or fully replace a relatively more expensive cement additive as discussed above. The cost of the cement composition may be improved by balancing the required engineering parameters such as compressive strength, mix ability, free water content, and others in order to maximize the amount of relatively lower cost silica based cement components. Any remaining deviation from the engineering requirement may be "made up" with the relatively more expensive cement additive. In this way, the cement composition may be reduced to a minimum cost per pound since the engineering requirements are met with a blend of primarily lower cost components.

Once the data is collected by the chosen laboratory techniques, categorized, and mapped, several operations may be performed on the data in order to yield predictions about a cement composition that comprises mapped cement components. Set properties, for example, may be estimated. A method of estimating the material reactivity based on the reactive index will be described below. Material reactivity may be based on many parameters such as specific surface area and specific gravity, among others. Another use for the mapped data may be to increase cement slurry performance based on parameters such as particle shape, particle size, and particle reactivity. The data may also be used to predict and capture slurry density dependence of compressive strength and use the insight gathered to design improved cement formulations. The data may also be used to predict a slurry composition to achieve an improved cement formulation. The criteria for just right may be compressive strength, cost, rheology, mechanical properties, fluid loss control properties, thickening times, and others.

Reactivity mapping may be used to estimate various mechanical properties of a cement component, including compressive strength, tensile strength, and Young's modulus. As previously described, correlations may be made between specific surface area and certain mechanical properties, such as reactivity, tensile strength, and Young's modulus. Using these correlations the mechanical properties for a cement component or combination of cement components may be predicted.

One technique that may be used to correlate reactivity and specific surface area is the reactive index. Without being limited by theory, the reactive index of a cement component may be referred to as a measure of the cement component's reactivity as adjusted for differences in surface area. It is important to note that the term "cement component" refers to any material that is cementitious when mixed with water and/or lime and a suspending agent, when necessary, such that the slurry is stable. A "cementitious reactive index" $CRI_i$ can be defined as, but not limited to, Equation [1] as follows:

$$CRI_i = f_{CRI}(CS_i, \rho_i, SSA_{PSDi}) \qquad [1]$$

Where:
$CS_i$=Unconfined UCS (ultimate compressive strength) obtained from samples cured at specific reference temperature, pressure and age.
$\rho_i$=Density of slurry that was prepared and cured for measuring UCS
$SSA_{PSDi}$=Specific surface area obtained by typical particle size analysis methods.

A "physicochemical index" (PCI) of the cementitious component may be defined as, but not limited to Equation [2]:

$$PCI_i = f_{PCI}(SA_i, SG_i, D_{50}, C_{Si}, C_{Ca}, C_{Al}, C_{Na}, C_{Fe}, C_{other\ species}) \qquad [2]$$

Where:
$SA_i$=Surface area of the cementitious component i,
$SG_i$=specific gravity of the cementitious component i,
$D_{50}$=mass average or volume average diameter of the particle size distribution of cementitious component i,
$C_{Si}$=Mass concentration of silica oxide of component i,
$C_{Ca}$=Mass concentration of calcium oxide of component i,
$C_{Al}$=Mass concentration of Aluminum oxide of component i,
$C_{Na}$=Mass concentration of sodium oxide of component i,
$C_{Fe}$=Mass concentration of iron oxide of component i, It should be noted that the mass concentrations referenced above and here to for, may be measured, but is not limited to X-ray fluorescence spectroscopy measuring technique and a reference to "component i" is equivalent to "cementitious component i". The functions in Equations [1] and [2] that define $CRI_i$ and $PCI_i$, when properly defined, the following universal relationship may hold for a wide range of cementitious materials such as, but not limited to, Portland cements; fly ash; other pozzolanic materials; other ashes; etc.

$$CRI_i = f_{CRI-PCI}(PCI_i) \qquad [3]$$

FIG. 1 is a graph of Equation [1] versus Equation [2] for real data, illustrating the accuracy of Equations [1], [2] and [3] when applied to five different types of cementitious material sources and three samples of similar materials but from different sources. The simulated data was found to have a relationship of $y=36.252x^{0.2256}$, wherein $R^2=0.9406$.

In some examples, the form of Equation [3] may be a power law, such as in Equation 4.

$$CRI_i = A\{PCI_i\}^B \qquad [4]$$

A and B are coefficients that may be unique the various species and sources of cementitious materials selected. Once the generalized function defined in Equation [4] is defined for a given population or group of cementitious components, a linear or nonlinear summation relationship further defined below, may be used in conjunction with Equation [5] to predict the UCS of various combinations of cementitious materials for specified slurry densities, temperatures, pressures and curing age.

$$CRI_c = A\{PCI_c\}^B \qquad [5]$$

Where,
$CRI_c$ is defined as the CRI for the unique combination of n cementitious components as the composite, and similarly
$PCI_c$ is defined as the Physicochemical Index for the composite.

A given composite with mass of $m_c$ is defined as:

$$m_c = f_i + f_{i+1} + f_{i+2} + f_n \qquad [6]$$

Where: $f_i$ is defined as the mass fraction of the cementitious component i, and n is the total number of independent cementitious components. Once the function is defined in Equation [5], then the composite value of the physicochemical reactive index may be computed using Equation [7] as follows:

$$PCI_c = f_1 PCI_1 + f_2 PCI_2 + f_3 PCI_3 + \ldots + f_n PCI_n \qquad [7]$$

Where: $PCI_c$ is defined as the overall chemical reactive index for a blend of n number of uniquely independent cementitious components, $f_i$ is defined as the mass fraction of the cementitious component i, and n is the total number of independent cementitious components. Once $PCI_c$ has been determined for specific assumed blend of selected cementitious components, then the linear or non-linear summations (Equations [8] and [9]) are determined for the following terms:

$$\rho_c = f_1 \rho_1 + f_2 \rho_2 + f_3 \rho_3 + \ldots + f_n \rho_n \qquad [8]$$

and, $$SSA_{PSDc} = f_1 SSA_{PSD1} + f_2 SSA_{PSD2} + f_3 SSA_{PSD3} + \ldots + f_n SSA_{PSDn} \qquad [9]$$

$PCI_c$ is used to compute the value of $CRI_c$ using either Equation [5] or the more generalized form of Equation [3] for the composite terms. Once $CRI_c$ is determined for the given composite blend, then the composite values of $\rho_c$ and $SSA_{PSDc}$ may be used along with Equation [10] to predict the actual compressive strength of the composite blend, $CS_c$.

$$CRI_c = f_{CRI}(CS_c, \rho_c, SSA_{PSDc}) \qquad [10]$$

Experimental data was collected for specific composite blends is summarized in the table below:

TABLE 1

| | Mass Fractions of Cementitious Components | | |
|---|---|---|---|
| Cementitious Component | Composite Blend 1 | Composite Blend 2 | Composite Blend 3 |
| A | 0.36 | | 0.53 |
| B | | 0.32 | |
| C | 0.32 | | 0.31 |
| D | | 0.33 | |
| E | 0.32 | | |
| F | | 0.35 | |
| G | | | 0.16 |
| Totals | 1.00 | 1.00 | 1.00 |

It is important to note that each of the cementitious components above were either distinctly different species (type) of cementitious composition and/or from a different source.

Figure 2:
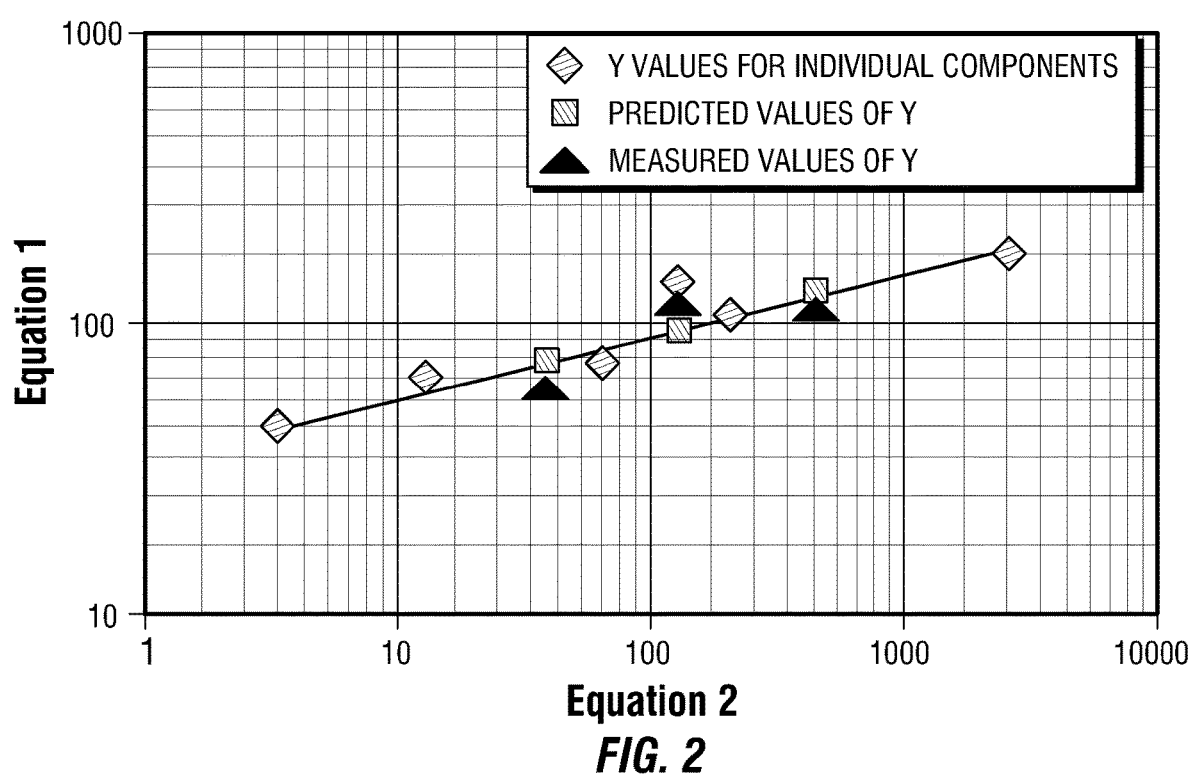
FIG. 2 is a chart showing simulated results for compressive strength index calculations.

FIG. 2 is another plot of Equation [1] versus Equation [2] for real data showing the accuracy of Equations [1], [2], and

[3]. Equations [1] through [10] may also be used for predicting other mechanical properties, including but not limited to, Young's Modulus of Elasticity and Tensile Strength. Additionally, it should be noted that even though a "linear summation" technique is presented in the previous development, that this invention also includes other methods such as the non-linear summation method presented in Equation [11].

$$PCI_c = (1+f_1)^{a1} PCI_1 + (1+f_2)^{a2} PCI_2 + (1+f_3)_{a3} PCI_3 + \ldots + (1+f_n)^{an} PCI_n \quad [11]$$

Where: ai are exponents that are determined for a unique set of cementitious components.

Further examples using the chemical reactive index, water requirement and other analytical parameters will now be discussed. A statistical table may be generated that plots chemical reactive index against water requirement. An example is shown in Table 2.

TABLE 2

Chemical Reactive Index Vs. Water Requirement

| Water Requirement | High | X1 | X4, X5 | X8 |
|---|---|---|---|---|
| | Medium | X2 | X6 | X9, X10 |
| | Low | X3 | X7 | X11 ... Xn |
| | | Low | Medium | High |
| | | | Chemical Reactive Index | |

Other analytical parameters such as particle size versus chemical reactive index, heat generation versus chemical reactive index, and others may also be used. By ranking the chemical reactive index against an analytical parameter, a blend of components may be selected that has a minimized cost and an improved chemical reactive index while still having a mixable composition. In some examples, a selected cement composition may have too much free water to set properly. In such examples, a component having a high water requirement may be selected to replace a component in the cement composition or supplement the cement composition. The selected component having the high water requirement may be selected based on the chemical reactive index to ensure that the overall blend has sufficient reactivity. A cement composition comprising the selected cement component may exhibit less free water due to the high water requirement of the component and may also exhibit the same reactivity from selecting the appropriate chemical reactive index. The reactivity of a cement composition may be tuned based on the selection of cement component having the desired reactivity. A component having a high reactivity may exhibit a faster set time that one with a low reactivity.

The reactivity of a cement composition may be affected by wellbore temperature. If a wellbore has a relatively low temperature, about <150° F. or less, a component having a relatively higher reactivity may be required to ensure that the cement composition develops adequate strength. In previous cement compositions, a chemical accelerator may have been used to enhance the reaction speed in a relatively lower temperature well. A cement composition comprising a relatively higher chemical reactive index component may not require an accelerator due to the high reactivity of the component. Cement compositions comprising a high reactivity component may not require an accelerator and therefore may have a lower overall cost. If a wellbore has a relatively high temperature, about >150° F. or greater, the cement component may be selected to have a relatively lower reactivity. Selecting a lower reactivity may be advantageous when the high temperature of a wellbore may cause the cement composition to set too quickly. In previous cement compositions, a cement set retarder may have been used to reduce the reaction speed in a relatively higher temperature well. By selecting a relatively lower reactivity component, the cement set reaction may potentially be slowed without the use of a retarder. The Selecting an appropriate cement component based on reactivity may reduce the cost of the cement composition by eliminating or reducing the need for accelerators and retarders. Furthermore, a combination of cement components may be blended to control the reactivity, for example by adding low, medium, and high reactivity cement components, a cement composition may be created that has a controlled reactivity along the spectrum of wellbore temperatures. One of ordinary skill in the art, with the benefit of this disclosure, should recognize the appropriate amount and type of cement component to include for a chosen application.

Another application of the previously mention statistical correlation may be in classifying cement components by cost among other factors. In general, the reactivity of a cement composition may be maximized to ensure that the cement composition will attain enough compressive strength to meet the design requirement of a particular well. If a specific cement composition far exceeds the engineering requirements, then an alternate cement composition comprising potentially less expensive components may be formulated. The following equations illustrate an improvement scheme for a cement composition.

$$CRI, \text{composite} = \sum (CRI_i * \% \text{ Concentration}) \quad [12]$$

$$\text{Cost Index, composite} = \sum (\text{Cost}_i * \% \text{ Concentration}) \quad [13]$$

$$\text{Optimized Blend} \rightarrow \max CRI, \quad [14]$$

composite $\wedge$ min Cost Index, composite $$\text{Optimization Ratio} = \max \left[ \frac{CRi, \text{composite}}{\text{Cost Index, composite}} \right] \quad [15]$$

Constraints: Cost Index < \$C, where $C \geq 0$ $CS = f(CRI, \text{analytical properies}) \rightarrow CS$, min < CS, composite < CS, max Using all the techniques previously discussed, a cement composition having a minimized cost and a maximized reactivity may be calculated. A first step may be to identify the engineering requirements of a particular well. Another step may be to define the inventory available at a particular field camp or well site. As previously mentioned, a particular region may have access to only a certain amount or kind of cement components. Some of the factors that may be considered in addition to those previously mentioned are the cost of goods sold, bulk density, and specific gravity for the available and potential inventory. The available cement components may be tested in a laboratory and classified using the methods previously discussed. Analytical study may comprise the various analytical techniques previously mentioned along with the physicochemical reactivity measurements for compressive strength, young's modulus, water requirement, and others. Next the correlations between the mechanical performance measures and analytical properties may be calculated. The chemical reactive index may also be calculated. A statistical table of the chemical reactive index and the water requirement may be calculated along with the chemical reactive index versus other selected analytical parameters.

An initial virtual design may be selected and tested to see if it meets the functional requirements defined by the engineering parameters. The initial virtual design may be based on a previous design, chosen from field experience, or selected by a computer. The virtual design may be based on, among other factors, the chemical reactivity of the cement components. If the virtual design meets all of the engineering parameters, a cost index for the composition may be calculated. The components of the cement composition may be adjusted iteratively until a cement composition having the maximum reactive index and minimized cost is achieved. In some examples, a fluid loss control additive, thickening additive, or other cement additives may be necessary to meet the functional requirements. As was previously described, the amount of cement additives that may need to be added to a cement composition may be minimized by selecting cement components that have inherent properties such as high reactive index, low water requirement, fluid loss control properties, and dispersive properties, among others.

As will be appreciated by those of ordinary skill in the art, the cement compositions disclosed herein may be used in a variety of subterranean applications, including primary and remedial cementing. The cement compositions may be introduced into a subterranean formation and allowed to set. As used herein, introducing the cement composition into a subterranean formation includes introduction into any portion of the subterranean formation, into near wellbore region surrounding the wellbore, or into both. In primary cementing applications, for example, the cement compositions may be introduced into the annular space between a conduit located in a wellbore and the walls of the wellbore (and/or a larger conduit in the wellbore), wherein the wellbore penetrates the subterranean formation. The cement composition may be allowed to set in the annular space to form an annular sheath of hardened cement. The cement composition may form a barrier that prevents the migration of fluids in the wellbore. The cement composition may also, for example, support the conduit in the wellbore. In remedial cementing applications, the cement compositions may be used, for example, in squeeze cementing operations or in the placement of cement plugs. By way of example, the cement compositions may be placed in a wellbore to plug an opening (e.g., a void or crack) in the formation, in a gravel pack, in the conduit, in the cement sheath, and/or between the cement sheath and the conduit (e.g., a microannulus).

While the present description refers to cement compositions and cement components, it should be understood that the techniques disclosed herein may be used with any suitable wellbore treatment composition and corresponding solid particulates of which cement compositions and cement components are one example. Additional examples of slurry compositions may include spacer fluids, drilling fluids, cleanup pills, lost circulation pills, and fracturing fluids, among others. In addition, while the preceding descriptions describes silica sources, it should be understood that present techniques may be used for mapping other suitable inorganic particulates.

Statement 1: A method comprising: analyzing each of a group of inorganic particles to generate data about physical and/or chemical properties of the inorganic particles; generating correlations between the inorganic particles based on the data.

Statement 2: The method of statement 1 further comprising generating a statistical table comprising two or more different parameters of the inorganic particles.

Statement 3: The method of statement 1 further comprising preparing a cement composition comprising the inorganic particles and allowing the cement composition to set in a wellbore.

Statement 4: The method of statement 1 wherein at least one of the inorganic particles comprises at least one of silica, alumina, iron, iron oxide, calcium, calcium oxide, sodium, potassium, magnesium, sulfur, and combinations thereof.

Statement 5: The method of statement 1 wherein the analyzing the inorganic particles comprises analysis by one or more techniques selected from the group consisting of microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological properties, Poisson's Ratio, API testing, and combinations thereof.

Statement 6: The method of statement 1 wherein the data comprises an amount of at least component selected from the group consisting of silica, alumina, iron, calcium, sodium, potassium, magnesium, sulfur, oxides thereof, and combinations thereof.

Statement 7: The method of statement 1 wherein the data comprises average particle size, particle size distribution, and morphology for each of the inorganic particles.

Statement 8: The method of particles 1 wherein the data comprises specific surface area for each of the inorganic particulates.

Statement 9: The method of statement 1 wherein the correlations comprises at least a correlation of specific surface area for each of the cement components to water requirement for each of the inorganic particles.

Statement 10: The method of statement 1 further comprising identifying a cement additive comprising two or more of the inorganic particles, and predicting one or more mechanical properties of a cement composition comprising the cement additive.

Statement 11: The method of statement 1 further comprising identifying a cement additive comprising two or more of the inorganic particles, and estimating reactivity of the cement additive.

Statement 12: The method of statement 1 further comprising identifying a cement additive comprising two or more of the inorganic particles, preparing a sample cement composition comprising the cement additive, testing the cement composition to determine one or more performance characteristics.

Statement 13: The method of statement 1 further comprising identifying a cement additive comprising two or more of the inorganic particles, based at least partially, on the correlations.

Statement 14: The method of any preceding statement further comprising mixing a wellbore treatment fluid comprising at least one of the inorganic particles using mixing equipment.

Statement 15: The method of statement 14 further comprising introducing the wellbore treatment fluid into a wellbore using one or more pumps.

Statement 16: A system comprising: a plurality of inorganic particles; an analytical instrument configured to gather physical and/or chemical data about the inorganic particles; a computer system configured to accept the physical and/or chemical data and/or generate correlations between properties of the inorganic particles based on the data.

Statement 17: The system of statement 16 wherein at least one of the inorganic particles comprises at least one of silica, alumina, iron, iron oxide, calcium, calcium oxide, sodium, potassium, magnesium, sulfur, and combinations thereof.

Statement 18: The system of statement 16 or statement 17 wherein the analytical instrument is configured to perform one or more of functions selected from the group consisting of microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological properties, Poisson's Ratio, API testing, and combinations thereof.

Statement 19: The system of any one or statements 16 to 18 wherein the computer system further comprises an algorithm configured to: analyze the physical and/or chemical data and output a predictive model; and store the predictive model in a predictive model database.

Statement 20: The system of statement 19 wherein the predictive model includes models of an effect other than a contribution to a cementitious reaction.

Statement 21: The system of statement 19 wherein the predictive model includes a correlation of a specific surface area and water requirement of at least one of the inorganic particles.

Statement 22: A system comprising: a predictive model database comprising predictive model data, correlations between properties, and raw data; a materials database; a computer system configured to query the predictive model database and the materials database and accept input from a user; and an algorithm capable of generating a calculated cement composition.

Statement 23: The system of statement 22 wherein the algorithm is configured to improve the calculated cement composition by generating a cement composition based on a cost objective of the calculated cement composition.

Statement 24: The system of statement 22 or 23 wherein the algorithm is configured to improve the calculated cement composition by selecting materials from the materials database.

Figure 3:
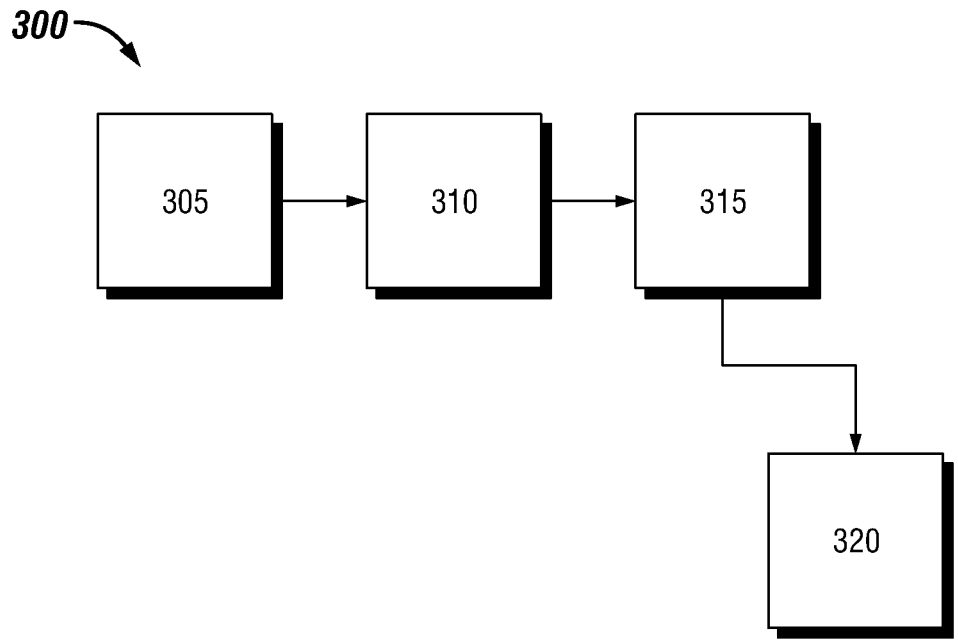
FIG. 3 is a schematic illustration of an example system for analyzing cement components.

Statement 25: The system of any one of statements 22 to 24 wherein the algorithm is configured to: analyze the input from the user; analyze the data from the predictive model database, the data comprising at least of the predictive model data, the correlations, and/or the raw data; and output the calculated cement composition Examples of the methods of using the reactivity mapping technique will now be described in more detail with reference to FIG. 3. A system 300 for analyzing the cement component is illustrated. The system 300 may comprise a cement component sample 305, analytical instrument 310, and computer system 315. Cement component sample 305 may be any cement component of interest. Cement components as previously described may be generally categorized as alkali soluble. The cement component sample may be placed or fed into analytical instrument 310. In some examples, analytical instrument 310 may be configured to automatically feed cement component sample 305 into analytical instrument 310. Analytical instrument 310 may be configured to analyze the physical and chemical properties of cement component sample 305. As previously described, physical and chemical properties may comprise without limitation, morphology, chemical composition, water requirement, and others. The data generated by analytical instrument 310 may be sent to computer system 315 for processing. Computer system 315 may comprise a processor, memory, internal storage, input and output means, network connectivity means, and/or other components common to computer systems. Computer system 315 may take the data from analytical instrument 310 as input and store it in the storage for later processing. Processing the data may comprise inputting the data into algorithms which compute a result. Processing the data may also comprise organizing the data and mapping the data as previously described. In particular, the computer system may comprise algorithms configured to process the data to generate a predictive model of the physical and chemical behavior of cement component sample 305. Predictive models may be stored in a predictive model database 320 which may be stored locally or on a network. The predictive model database 320 may comprise all previous predictive models generated by the algorithms as well as maps of the generated data as well as the raw data.

Figure 4:
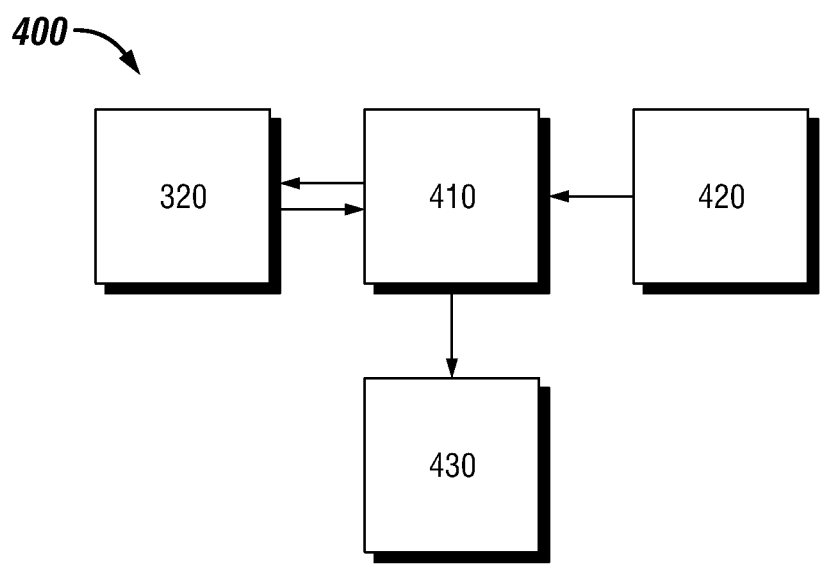
FIG. 4 is a schematic illustration of an example system for generating cement compositions.

Referring now to FIG. 4, a system 400 for generating cement compositions is illustrated. The system 400 may comprise a predictive model database 320 and computer system 410. In some examples, computer system 410 may be the same computer system 315 of FIG. 3. A user input 420 may define engineering parameters such as the required compressive strength of a cement slurry, the bottom hole static temperature of the wellbore, the required rheological properties of the slurry, the thickening time of the slurry, cement materials, cement additives, free fluid, permeability, pore pressure, fracture gradient, mud weight, density, acid resistance, salt tolerance, and other parameters. Computer system 410 may be configured to input user input 420 and the predictive models, maps, and data stored in predictive model database 320 into a predictive cement algorithm. The predictive cement algorithm may generate a cement composition or compositions that meet the engineering requirements define by the user input 420. The output 430 of the predictive cement algorithm may contain the relative amounts of each cement component in the generated cement composition as well as the predicted material properties of the cement composition.

For example, if a user selects Portland cement, fly ash, and volcanic rock as the cement materials available the computer system may query predictive model database 320 for the required models, maps, and data corresponding to the cement materials. As previously described, there may be many different parameters such as particle size, regional source of the cement material, among others that may determine which set of data that is retrieved from predictive model database 320. The predictive cement algorithm may be configured to improve the output cement slurry based on one or more parameters such as cost, compressive strength, or any other chosen parameter. In some examples the predictive cement algorithm may optimize on two or more variable. Optimize in this context should not be understood as arriving at a best result but rather that the cement algorithm is configured to iterate on one or more variables.

The output of the algorithm in this example may be for example, 30% Portland by weight, 30% volcanic rock by weight, 20% fly ash, and 20% lime, with a 120% excess by weight of water. The generated slurry may conform within a margin of error to the engineering parameters supplied by user input 420. The generated slurry may be added to predictive model database 320 to be used in future calculations.

As previously discussed, the cement components may have secondary effects such as gelling, dispersive properties, heat generation, and other secondary effects previously mentioned in addition to the primary effect of being cementitious when included in a cement composition. The secondary effects may be beneficial as well. For example, if a cement composition requires a thickening agent, instead of using a separate additive to thicken the cement composition, a cement component that gels may be used in the place of another additive. Other secondary effects may also be taken advantage of in a similar manner. The predictive cement algorithm may calculate the secondary effects of each component in the cement slurry and adjust the relative amounts of each component to ensure the target parameters are met. User input 420 may specify, for example, a relatively higher free water requirement for the cement slurry. The predictive cement algorithm may choose to include a cement component that requires less water based on the maps and data to ensure that the free water requirement specified by user input 420 is met.

Figure 5:
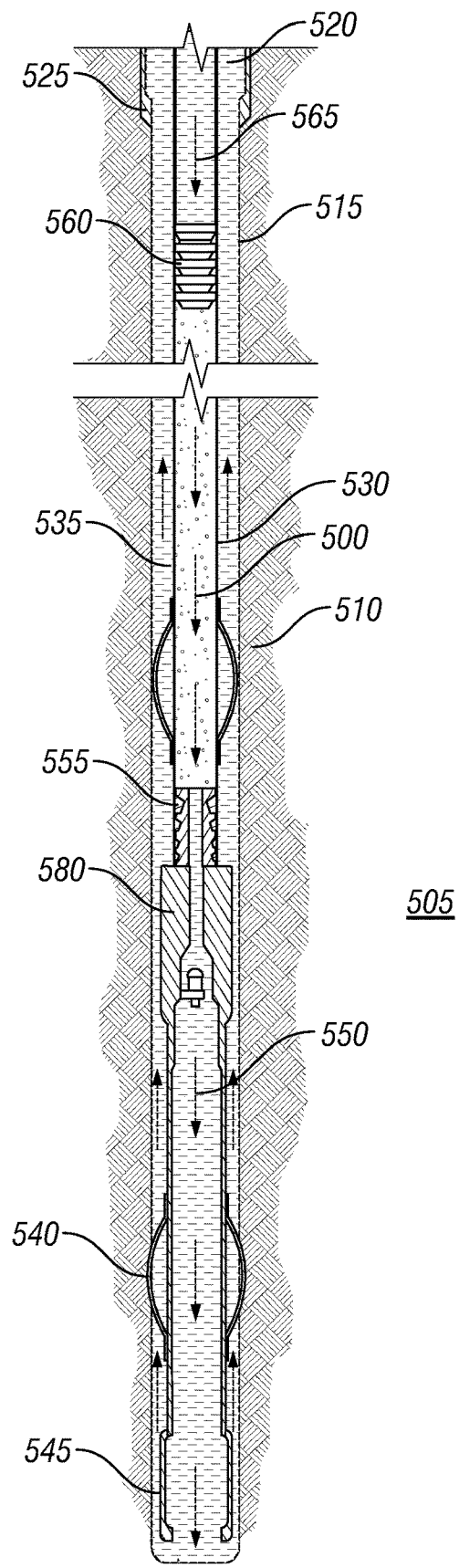
FIG. 5 is a schematic illustration of showing introduction of a cement composition into a wellbore.

Reference is now made to FIG. 5, illustrating use of a cement composition 500. Cement composition 500 may comprise any of the components described herein. Cement composition 500 may be designed, for example, using reactivity mapping as described herein. Turning now to FIG. 5, the cement composition 500 may be placed into a subterranean formation 505 in accordance with example systems, methods and cement compositions. As illustrated, a wellbore 510 may be drilled into the subterranean formation 505. While wellbore 510 is shown extending generally vertically into the subterranean formation 505, the principles described herein are also applicable to wellbores that extend at an angle through the subterranean formation 505, such as horizontal and slanted wellbores. As illustrated, the wellbore 510 comprises walls 515. In the illustration, a surface casing 520 has been inserted into the wellbore 510. The surface casing 520 may be cemented to the walls 515 of the wellbore 510 by cement sheath 525. In the illustration, one or more additional conduits (e.g., intermediate casing, production casing, liners, etc.), shown here as casing 530 may also be disposed in the wellbore 510. As illustrated, there is a wellbore annulus 535 formed between the casing 530 and the walls 515 of the wellbore 510 and/or the surface casing 520. One or more centralizers 540 may be attached to the casing 530, for example, to centralize the casing 530 in the wellbore 510 prior to and during the cementing operation.

With continued reference to FIG. 5, the cement composition 500 may be pumped down the interior of the casing 530. The cement composition 500 may be allowed to flow down the interior of the casing 530 through the casing shoe 545 at the bottom of the casing 530 and up around the casing 530 into the wellbore annulus 535. The cement composition 500 may be allowed to set in the wellbore annulus 535, for example, to form a cement sheath that supports and positions the casing 530 in the wellbore 510. While not illustrated, other techniques may also be utilized for introduction of the cement composition 500. By way of example, reverse circulation techniques may be used that include introducing the cement composition 500 into the subterranean formation 505 by way of the wellbore annulus 535 instead of through the casing 530. As it is introduced, the cement composition 500 may displace other fluids 550, such as drilling fluids and/or spacer fluids that may be present in the interior of the casing 530 and/or the wellbore annulus 535. While not illustrated, at least a portion of the displaced fluids 550 may exit the wellbore annulus 535 via a flow line and be deposited, for example, in one or more retention pits. A bottom plug 355 may be introduced into the wellbore 510 ahead of the cement composition 500, for example, to separate the cement composition 500 from the fluids 550 that may be inside the casing 530 prior to cementing. After the bottom plug 555 reaches the landing collar 580, a diaphragm or other suitable device should rupture to allow the cement composition 500 through the bottom plug 555. The bottom plug 555 is shown on the landing collar 580. In the illustration, a top plug 560 may be introduced into the wellbore 510 behind the cement composition 500. The top plug 360 may separate the cement composition 500 from a displacement fluid 565 and also push the cement composition 500 through the bottom plug 555.

The disclosed cement compositions and associated methods may directly or indirectly affect any pumping systems, which representatively includes any conduits, pipelines, trucks, tubulars, and/or pipes which may be coupled to the pump and/or any pumping systems and may be used to fluidically convey the cement compositions downhole, any pumps, compressors, or motors (e.g., topside or downhole) used to drive the cement compositions into motion, any valves or related joints used to regulate the pressure or flow rate of the cement compositions, and any sensors (i.e., pressure, temperature, flow rate, etc.), gauges, and/or combinations thereof, and the like. The cement compositions may also directly or indirectly affect any mixing hoppers and retention pits and their assorted variations.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present disclosure is well adapted to attain the ends and advantages mentioned as well as those that are inherent therein. The particular examples disclosed above are illustrative only, as the present invention may be modified and practiced in different but equivalent manners apparent to those skilled in the art having the benefit of the teachings herein. Although individual examples are discussed, the invention covers all combinations of all those examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed is:

1. A method comprising:
   measuring properties of each of a group of inorganic particles to generate data about physical and/or chemical properties of the inorganic particles; and
   analyzing the data, wherein the analyzing comprises generating correlations between the measured properties of the inorganic particles based on the data and categorizing the inorganic particles according to either the measured properties and/or to properties estimated by the correlations, wherein the correlations comprise at least a water requirement as a function of specific surface area, wherein the water requirement is determined by a process comprising: preparing a blender with a specified amount of water; agitating the water at a specified rate; adding a powdered solid comprising one or more of the inorganic particles to the water until a specified consistency is obtained; and calculating the water requirement based on a ratio of the amount of water to an amount of the powdered solid required to reach the specified consistency.

2. The method of claim 1 further comprising generating a statistical table comprising two or more different parameters of the inorganic particles.

3. The method of claim 1 further comprising preparing a cement composition comprising the inorganic particles and allowing the cement composition to set in a wellbore.

4. The method of claim 1 wherein at least one of the inorganic particles comprises at least one of silica, alumina, iron, iron oxide, calcium, calcium oxide, sodium, potassium, magnesium, sulfur, and combinations thereof.

5. The method of claim 1 wherein the measuring properties of the inorganic particles comprises analysis by at least one techniques selected from the group consisting of x-ray diffraction, x-ray fluorescence, scanning electron microscopy, energy dispersive spectroscopy, thermogravimetric analysis, and any combinations thereof.

6. The method of claim 1 wherein the data comprises an amount of at least one component selected from the group consisting of silica, alumina, iron, calcium, sodium, potassium, magnesium, sulfur, oxides thereof, and combinations thereof.

7. The method of claim 1 wherein the data comprises average particle size, particle size distribution, and morphology for each of the inorganic particles.

8. The method of claim 1 further comprising identifying a cement additive comprising two or more of the inorganic particles and predicting one or more mechanical properties of a cement composition comprising the cement additive.

9. The method of claim 1 further comprising identifying a cement additive comprising two or more of the inorganic particles and estimating reactivity of the cement additive.

10. The method of claim 1 further comprising identifying a cement additive comprising two or more of the inorganic particles, preparing a sample cement composition comprising the cement additive, testing the cement composition to determine one or more performance characteristics.

11. The method of claim 1 further comprising identifying a cement additive comprising two or more of the inorganic particles, based at least partially, on the correlations.

12. The method of claim 1, wherein the group of inorganic particles comprises volcanic rock.

13. The method of claim 1, wherein the group of inorganic particles comprises a metal silicate.

14. The method of claim 1, wherein the inorganic particles are further categorized by silica content, calcium oxide content, alumina content, and by at least one other oxide content, wherein the other oxide content is determined from an oxide analysis performed using an analytical instrument.

15. A method comprising:
   measuring properties of each of a group of inorganic particles to generate data about physical and/or chemical properties of the inorganic particles, wherein the data comprises average particle size, particle size distribution, and morphology for each of the inorganic particles, and wherein the morphology comprises at least one value or description corresponding to either the sphericity, roundness, or general shape of the inorganic particles; and
   analyzing the data, wherein the analyzing comprises generating correlations between the measured properties of the inorganic particles based on the data and categorizing the inorganic particles according to either the measured properties or to properties estimated by the correlations, wherein the correlations comprise at least a water requirement as a function of specific surface area, wherein the water requirement is determined by a process comprising: preparing a blender with a specified amount of water; agitating the water at a specified rate; adding a powdered solid comprising one or more of the inorganic particles to the water until a specified consistency is obtained; and calculating the water requirement based on a ratio of the amount of water to an amount of the powdered solid required to reach the specified consistency.

16. The method of claim 15, further comprising providing an estimate of a performance characteristic wherein the estimated performance characteristic is either material reactivity, fluid loss control ability, or dispersing ability.

17. The method of claim 16, wherein the measuring comprises performing at least one measurement technique selected from the list consisting of particle size analysis, specific gravity analysis, specific surface area analysis, compressive strength analysis, morphology analysis, and water requirement analysis.

18. A method comprising:
   measuring one or more physicochemical properties of each species of a group of inorganic particles to generate physical and/or chemical data about the inorganic particles;
   measuring one or more physicochemical properties of a waste material to generate physical and/or chemical data about the waste material;
   analyzing the data, wherein the analyzing comprises generating correlations between variables and categorizing the inorganic particles and waste material according to the variables, wherein the variables comprise one or more measured properties and one or more properties estimated by the correlations, wherein the correlations comprise at least a water requirement as a function of specific surface area, wherein the water requirement is determined by a process comprising:
preparing a blender with a specified amount of water;
agitating the water at a specified rate;
adding a powdered solid to the water until a specified consistency is obtained; and
calculating the requirement based on a ratio of the amount of water to an amount of the powdered solid required to reach the specified consistency;
querying a predictive model database to retrieve a predictive model, wherein the querying is based at least in part on a user input engineering parameter, wherein the predictive model is based on an iterating on two or more of the variables, and wherein the predictive model accounts for a secondary effect of the inorganic particles; and
outputting relative amounts of each cement component in a cement slurry comprising a plurality of cement components based at least in part on an output of the predictive model, wherein at least one of the cement components comprises one or more of the inorganic particles; and
predicting a performance characteristic of a cement based, at least partially, on the output of the predictive model and the measured or estimated properties, wherein the cement comprises the waste material and one or more of the inorganic particles.

19. The method of claim 18, wherein the performance characteristic comprises at least one mechanical property selected from the group consisting of compressive strength, tensile strength, Young's modulus of elasticity, and any combination thereof.

20. The method of claim 18 wherein the measuring comprises performing at least one measurement technique selected from the list consisting of specific surface area analysis, morphology analysis, water requirement analysis, specific gravity analysis, thermogravimetric properties analysis, particle shape analysis, particle size analysis, particle size distribution analysis, dispersing ability analysis, thickening time analysis, 24 hour compressive strength analysis, fluid loss analysis, and any combination thereof.

21. The method of claim 18, further comprising specifying a desired performance characteristic of the cement and selecting one or more cementitious components based, at least in part, on the predicted performance characteristic, wherein the cement additionally comprises the one or more cementitious components.

22. The method of claim 18, wherein the performance characteristic comprises at least one property selected from the list consisting of slurry density, average specific gravity, pressure, curing age, water requirement, dispersing ability, thickening time, reactivity, heat generation, and any combination or derivative thereof.

23. The method of claim 18, wherein the secondary effect of the cement component is gelling.

24. The method of claim 18, wherein the secondary effect of the cement component is dispersing ability.

25. The method of claim 18, wherein the user input engineering parameter is a gelling rate.

\* \* \* \* \*